United States Patent [19]

Okada et al.

[11] Patent Number: 4,968,805
[45] Date of Patent: Nov. 6, 1990

[54] PYRAZOLE DERIVATIVES AND INSECTICIDAL FUNGICIDAL AND MITICIDAL COMPOSITIONS THEREOF

[75] Inventors: Itaru Okada, Kanagawa; Shigeru Suzuki, Yokohama; Shuko Okui, Tokyo; Yoji Takahashi, Machida; Toshiki Fukuchi; Tetsuo Nakajima, both of Yokohama, all of Japan

[73] Assignee: Mitsubishi Kasei Corporation, Tokyo, Japan

[21] Appl. No.: 310,591

[22] Filed: Feb. 15, 1989

[30] Foreign Application Priority Data

Feb. 16, 1988 [JP] Japan .................................. 63-33383
May 18, 1988 [JP] Japan ................................. 63-121295

[51] Int. Cl.$^5$ .................... C07D 231/14; C07D 231/54
[52] U.S. Cl. ...................................... 546/271; 546/279
[58] Field of Search ................ 546/271, 279; 514/338, 514/341

[56] References Cited

U.S. PATENT DOCUMENTS

| | | | |
|---|---|---|---|
| 3,457,269 | 7/1969 | Kirchner | 546/271 |
| 3,875,182 | 4/1975 | Bretschneider | 548/374 |
| 3,937,822 | 2/1976 | DeLong | 514/23 |
| 4,005,100 | 1/1977 | Bretschneider | 548/374 |
| 4,495,195 | 1/1985 | Beck | 514/406 |
| 4,861,777 | 8/1989 | Okada | 514/234.5 |

FOREIGN PATENT DOCUMENTS

| | | |
|---|---|---|
| 47-6269 | 6/1972 | Japan . |
| 48-56671 | 3/1973 | Japan . |
| 56-73071 | 2/1981 | Japan . |
| 60-34902 | 2/1985 | Japan . |
| 64-25763 | 1/1989 | Japan . |
| 01156964 | 6/1989 | Japan . |

OTHER PUBLICATIONS

*J. Phar. Sci.*, vol. 74, No. 9, Sep. 1985, pp. 1013-1015, "Synthesis of Anti-Inflammatory . . . ".
Rev. Roum. Chem., vol. 23, (1978), pp. 1581-1588, "Some Reactions of B-Aroyl-Acrylic Acid Epoxides", M. A. El-Hashash and M. El-Kady.
Pest. Bio. Phy., vol. 25, (1986), pp. 163-168, "Pyrazole Carboxanilide Fungicides", White et al.

*Primary Examiner*—Mary C. Lee
*Assistant Examiner*—Jacqueline Haley
*Attorney, Agent, or Firm*—Oblon, Spivak, McClelland, Maier & Neustadt

[57] ABSTRACT

Disclosed herein are pyrazole derivatives which are represented by the following formula (I):

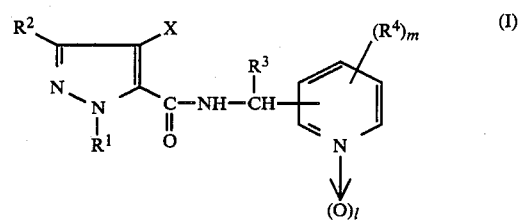

wherein $R^1$ represents a $C_1$-$C_4$ alkyl group or a benzyl group; $R^2$ represents a hydrogen atom or a $C_1$-$C_4$ alkyl group; X represents a hydrogen atom, a halogen atom or a $C_1$-$C_4$ alkyl group; $R^2$ may combine with X to form

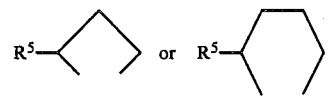

wherein $R^5$ represents a hydrogen atom or a $C_1$-$C_3$ alkyl group; $R^3$ represents a hydrogen atom or a $C_1$-$C_4$ alkyl group; $R^4$s independently represent a hydrogen atom, a halogen atom, a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group, a phenyl group, an alkyl-substituted phenyl group or

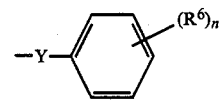

wherein Y represents an oxygen atom or a sulfur atom, $R^6$s independently represent a hydrogen atom, a $C_1$-$C_4$ alkyl group, a $C_1$-$C_4$ alkoxy group, a halogen atom, a nitro group, a cyano group or a trifluoromethyl group and n represents 1 or 2, adjacent $R^4$s being able to combine together to form

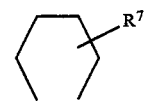

wherein $R^7$ represents a hydrogen atom or a methyl group; l represents 0 or 1; and m represents 1, 2, or 3. The pyrazole derivatives of the formula (I) show a high activity suitable for active ingredient of insecticidal and miticidal composition as well as fungicidal composition.

7 Claims, No Drawings

PYRAZOLE DERIVATIVES AND INSECTICIDAL FUNGICIDAL AND MITICIDAL COMPOSITIONS THEREOF

BACKGROUND OF THE INVENTION

The present invention relates to a novel pyrazole derivative, an insecticidal and miticidal composition containing the derivative as an active ingredient and a fungicidal composition containing the derivative as an active ingredient.

Examples of compounds having similar structures to that of the pyrazole derivative of the present invention include the compounds described in Pest. Bio. Phy., 25, 163 (1986) and Japanese Patent Laid-Open (KOKAI) Nos. 52-87168 (1977) and 60-34949 (1985) which each have fungicidal activity; the compound described in Japanese Patent Laid-Open (KOKAI) No. 57-106665 (1982) which has herbicidal activity and the compounds respectively described in Japanese Patent Laid-Open (KOKAI) Nos. 47-6269 (1972), 48-56671 (1973), 52-83840 (1977), 56-73071 (1981) and 59-95272 (1984), Japanese Patent Publication No. 55-44751 (1980) and J. Pharm. Sci., 74, 1013 (1985) which each have medicinal activity. However, there is no description with respect to insecticidal and miticidal activities. None of the above-described publications and literature also describes an aralkyl group as a substituent for the amide moiety of the compound.

On the other hand, Farmaco. Ed. Sci., 22, 692 (1967) describes N-benzyl-3-methyl-5-pyrazolecarboxamide and benzyl 3-methyl-5-pyrazolecarboxylate, Rev. Roum. Chim., 23, 1581 (1978) describes N-benzyl-1-(2,4-dinitrophenyl)-3-biphenyl-5-pyrazolecarboxamide, and Japanese Patent Laid-Open (KOKAI) No. 50-58056 describes N-(4-hydroxybenzyl)-1,3-dimethyl-5-pyrazolecarboxamide and N-(4-hydroxycarbonylmethoxybenzyl)1,3-dimethyl-5-pyrazolecarboxamide.
However, none of these reports describes the presence of insecticidal, miticidal and fungicidal activities of the compounds disclosed therein.

Although it has been described in Japanese Patent Laid-Open (KOKAI) Nos. 63-246367 (1988) and 63-135364 (1988) that N-(α-cyanobenzyl)-5-pyrazolecarboxamides have fungicidal activity, the compound disclosed therein is characterized by the cyano group on the α-position of the benzyl group. In Japanese Patent Laid-Open (KOKAI) No. 63-91373 (1988), N-(alkyl, substituted or non-substituted phenyl or benzyl)-1-(substituted or non-substituted phenyl)-5-pyrazolecarboxamide has been proposed as a plant growth regulator or a toxicity mitigator.

Japanese Patent Laid-Open (KOKAI) No. 62-120369 (1987) discloses N-(substituted or non-substituted benzyl)-1-(substituted phenyl)-4-(nitro or cyano)-5-pyrazolecarboxamides. The compound disclosed therein is characterized to have a nitro group or a cyano group as the substituent on the 4-position of the pyrazole ring, however, any examples of N-(substituted or non-substituted benzyl)-5-pyrazolecarboxamide have not been described therein.

Japanese Patent Laid-Open (KOKAI) No. 63-258859 (1988) discloses N-(substituted or non-substituted aralkyl)-1-(substituted phenyl)-4-(substituted thio, substituted sulfoxy or substituted sulfonyl)-5-pyrazolecarboxamides. Although these compounds are characterized by having a substituted thio group, a substituted sulfoxy group or a substituted sulfonyl group as the substituent on the 4-position, any examples of N-(substituted or non-substituted aralkyl)-5-pyrazolecarboxamides have not been described therein.

Synthesis, 727 (1981); Farmaco, Ed.Sci., 38, 369 (1983) and J. Med.Chem., 27, 986 (1984) disclose that N-(substituted or non-substituted benzyl)-3-methyl-4-nitro-5-pyrazolecarboxamide has medicinal activity.

Japanese Patent Publication (KOKOKU) No. 48-15300 (1973) discloses that N-(dibenzyl or dialkyl)-3-methyl-5-pyrazolecarboxamide has medicinal activity.

Although Japanese Patent Application No. 63-53165 (1988) and Japanese Patent Application No. 63-175450 (1988) disclose compounds having similar structures to those of the compounds of the present invention, only aralkyl such as benzyl and naphthylmethyl which may have substituents are disclosed as a substituent for the amide moiety.

The examples in which the substituent for the amide moiety is aralkyl have been described in detail as above.

As the compound in which the substituent for the amide moiety contains a hetero ring, N-(2-chloro-3-pyridyl)-1,3-dimethyl-4-nitro-5-pyrazolecarboxamide (Ger. Offen. DE 3,122,670) and N-pyridyl-3-methyl-5-pyrazolecarboxamide (Japanese Patent Laid-Open (KOKAI) No. 54-9278 (1979) are mentioned. In these compounds, the substituent for the amide moiety is a pyridyl group, and there is no description about insecticidal activity, miticidal activity and fungicidal activity of the compounds.

Japanese Patent Laid-Open (KOKAI) Nos. 63-246367 (1988) and 63-119463 (1988) disclose that the compound in which the substituent for the amide moiety is a hetero ring substituted methyl group, such as N-(α-cyanothienylmethyl)-1,3-dimethyl-5-pyrazolecarboxamide, shows fungicidal activity. However, any of the hetero ring substituted methyl groups in the compound disclosed therein has a cyano group at α-position thereof and a pyridylmethyl group is not disclosed therein as the hetero ring substituted methyl group.

The compounds disclosed in the prior publication have been given above in detail, however, the compound in which the acid moiety is a pyrazole and the substituent for the amide moiety is a pyridylmethyl group has not been reported.

Since harmful insects have recently had resistance to insecticides due to use of insecticides for many years, it has been difficult to control insects by conventional insecticides. For example, insect having resistance to organophosphorous compounds and carbamate compounds which are both typical insecticides have been widely generated, resulting in the difficulty of control of these insects. In addition, the presence of insects having the resistance to synthetic pyrethloid-type insecticides which have recently attracted attention has been reported. On the other hand, some of the organophosphorous compounds or carbamate compounds exhibit high toxicity, and some of them disturb the ecological system due to their high residual effect to bring about an extremely anxious problem. Therefore, it is expected to develop a novel insecticide which exhibits an excellent controlling effect even against insects and mites having resistance to conventional insecticides and which has low toxicity and low residual effect.

The controlling effect of fungicides for agricultural and horticultural use has been reduced also by the generation of fungus which has gained resistance to the conventional fungicides, and accordingly, the development of a novel fungicide has been expected.

As a result of the investigations performed by the present inventors for solving such a problem, a novel pyrazole derivative which has excellent insecticidal, miticidal and fungicidal activities has been found.

The present invention has been accomplished based on this finding.

SUMMARY OF THE INVENTION

In a first aspect of the present invention, there are provided pyrazole derivatives represented by the following formula (I):

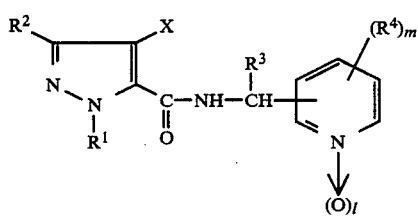

wherein $R^1$ represents a $C_1$–$C_4$ alkyl group or a benzyl group; $R^2$ represents a hydrogen atom or a $C^1$–$C_4$ alkyl group; X represents a hydrogen atom, a halogen atom or a $C_1$–$C_4$ alkyl group; $R^2$ may combine with X to form

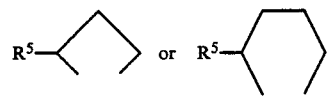

wherein $R^5$ represents a hydrogen atom or a $C_1$–$C_3$ alkyl group; $R^3$ represents a hydrogen atom or a $C_1$–$C_4$ alkyl group; $R^4$s independently represent a hydrogen atom, a halogen atom, a $C_1$–$C_5$ alkyl group, a $C_1$–$C_4$ alkoxy group, a $C_1$–$C_4$ alkylthio group, a trifluoromethyl group, a $C_1$–$C_4$ haloalkoxy group, a phenyl group, an alkyl-substituted phenyl group or

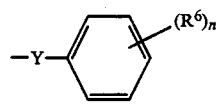

wherein Y represents an oxygen atom or a sulfur atom, $R_6$s independently represent a hydrogen atom, a $C_1$–$C_4$ alkyl group, a $C_1$–$C_4$ alkoxy group, a halogen atom, a nitro group, a cyano group or a trifluoromethyl group and n represents 1 or 2, adjacent $R^4$s being able to combine together to form

wherein $R^7$ represents a hydrogen atom or a methyl group; l represents 0 or 1; and m represents 1, 2 or 3.

In a second aspect of the present invention, there is provided an insecticidal and miticidal composition comprising an insecticidally and miticidally effective amount of the pyrazole derivative of the formula (I) as an active ingredient.

In a third aspect of the present invention, there is provided a fungicidal composition comprising a fungicidally effective amount of the pyrazole derivative of the formula (I) as an active ingredient.

In a fourth aspect of the present invention, there is provided a process for producing the pyrazole derivative of the formula (I).

DETAILED DESCRIPTION OF THE INVENTION:

In the formula (I), $R^1$ is a straight or branched $C_1$–$C_4$ alkyl such as methyl group, ethyl group, n-propyl group, isopropyl group, n-butyl group, isobutyl group, sec-butyl group, t-butyl group, or a benzyl group, and preferably a methyl.

$R^2$ represents a hydrogen atom or a straight or branched $C_1$–$C_4$ alkyl group such as methyl group, ethyl group, n-propyl group, isopropyl group, n-butyl group, isobutyl group, sec-butyl group, t-butyl group, and preferably a hydrogen atom or a straight or branched $C_1$–$C_3$ alkyl group such as methyl group, ethyl group, n-propyl group, isopropyl group.

X is a hydrogen atom, a halogen atom such as fluorine atom, chlorine atom, bromine atom, iodine atom, etc. or a straight or branched $C_1$–$C_4$ alkyl group such as methyl group, ethyl group, n-propyl group, isopropyl group, n-butyl group, isobutyl group, sec-butyl group, t-butyl group, and preferably a hydrogen atom, a halogen atom such as fluorine atom, chlorine atom, bromine atom, etc., methyl group or ethyl group.

The above $R^2$ and X may combine together to form a divalent group represented by the formula of

wherein $R^5$ represents a hydrogen atom or a $C_1$–$C_3$ alkyl group such as methyl group, ethyl group, n-propyl group and isopropyl group, and preferably a hydrogen atom or a methyl group.

$R^3$ is a hydrogen atom or a straight or branched $C_1$–$C_4$ alkyl group such as methyl group, ethyl group, n-propyl group, isopropyl group, n-butyl group, isobutyl group, sec-butyl group, t-butyl group, preferably a hydrogen atom or a methyl group.

$R^4$ is a hydrogen atom; a halogen atom such as fluorine atom, chlorine atom, bromine atom, iodine atom, etc.; a straight or branched $C^1$–$C_5$ alkyl group such as methyl group, ethyl group, n-propyl group, isopropyl group, n-butyl group, isobutyl group, sec-butyl group, t-butyl group, n-amyl group, isoamyl group, t-pentyl group and neopentyl group; a straight or branched $C_1$–$C_4$ alkoxy group such as methoxy group, ethoxy group, n-propoxy group, isopropoxy group, n-butoxy group, isobutoxy group, sec-butoxy group and t-butoxy group; a straight or branched $C_1$–$C_4$ alkylthio group such as methylthio group, ethylthio group, n-propylthio group, isopropylthio group, n-butylthio group, isobutylthio group, sec-butylthio group and t-butylthio group; a trifluoromethyl group; a straight or branched $C_1$–$C_4$ haloalkoxy group such as difluoromethoxy group, trifluoromethoxy group, 2-fluoroethoxy group, 2-chloroethoxy group, 2,2,2-trifluoroethoxy group, 2,2,2-trichloroethoxy group, 3-chloropropoxy group, 3-bromopropoxy group, 3,3,3-trifluoropropoxy group, 2,2,3,3-tetrafluoropropoxy group, 2,2,3,3,3-pentafluoropropoxy group, 2,2-dichloro-3,3,3-trifluoropropoxy group, 1-trifluoromethylethoxy group, 1,3-difluoro-2-propoxy group, 1,1,1,3,3,3-hexafluoro-2-propoxy group, 3,3,3-trichloropropoxy group, 4-chlorobutoxy group, 4,4,4-trifluorobutoxy group, 3,3,4,4,4-pentafluorobutoxy group, 2,2,3,3,4,4-hexafluorobutoxy group, 2,2,3,4,4,4-hexafluorobutoxy group, 2,2,3,3,4,4,4-heptafluorobutoxy group, 1-trifluoromethylpropoxy group, 1,1,1,2,2-pentafluoro-3-butoxy group, etc.; a phenyl group; a phenyl group substituted by a $C_1$–$C_4$ alkyl group such as methyl, ethyl, n-propyl, isopropyl, n-butyl, isobutyl, sec-butyl and t-butyl group; or

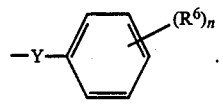

In the formula

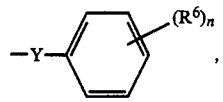

Y is an oxygen atom or a sulfur atom; $R^6$ is a hydrogen atom, a straight or branched $C_1$–$C_4$ alkyl group such as methyl group, ethyl group, n-propyl group, isopropyl group, n-butyl group, isobutyl group, sec-butyl group and t-butyl group, a $C_1$–$C_4$ alkoxy group such as methoxy group, ethoxy group, n-propoxy group, isopropoxy group, n-butoxy group, isobutoxy group, sec-butoxy group and t-butoxy group, a halogen atom such as fluorine atom, chlorine atom, bromine atom, iodine atom, etc., a nitro group, a cyano group or a trifluoromethyl group; and n is 1 or 2. When n is 2, two $R^6$s may be either the same or different groups.

"l" represents 0 or 1.

"m" represents 1, 2 or 3. When m is 2 or 3, two or three $R^4$s may be either the same or respectively different groups and adjacent $R^4$s can combine together to form a divalent group represented by the formula of

wherein $R^7$ represents a hydrogen atom or a methyl group.

Of the pyrazole derivatives represented by the formula (I), the preferred compounds as the active ingredient of insecticidal and miticidal composition are those wherein $R^1$ is a methyl group; $R^2$ is a hydrogen atom or a $C_1$–$C_3$ alkyl group; X is a hydrogen atom or a halogen atom, or $R_2$ and X combine together to form

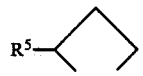

wherein $R^5$ is a hydrogen atom or a methyl group; $R^3$ is a hydrogen atom; $R^4$ is a $C_1$–$C_5$ alkyl group, a $C_1$–$C_4$ alkoxy group, a $C_1$–$C_4$ alkylthio group, a trifluoromethyl group, a $C_1$–$C_4$ haloalkoxy group or a

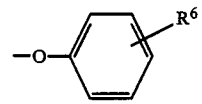

wherein $R_6$ is a halogen atom or a trifluoromethyl group; l is 0; and m is 1 or 2.

Further preferred compounds are those wherein $R^1$ is a methyl group; $R^2$ is a hydrogen atom, a methyl group or an ethyl group; X is a fluorine atom, a chlorine atom or a bromine atom, or $R^2$ combines together with X to form

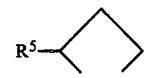

wherein $R^5$ is a hydrogen atom or a methyl group; $R^3$ is a hydrogen atom; $R^4$ is an n-butyl group, t-butyl group, 2,2,2-(trifluoroethoxy group, 3,3,3-trifluoropropoxy group, 2,2,3, 4,4,4-hexafluorobutoxy group, 1-trifluoromethylethoxy group or 4-trifluoromethylphenoxy group; l is 0; and m is 1.

Of the pyrazole derivatives represented by the formula (I), the preferred compounds as the active ingredient of fungicidal composition are those wherein $R^1$ is a methyl group; $R^2$ and X combine together to form

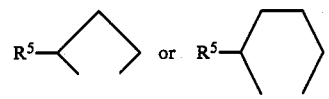

wherein $R^5$ is a hydrogen atom or a methyl group; $R^3$ is a hydrogen atom; $R^4$ is a $C_1$–$C_5$ alkyl group, a $C_1$–$C_4$ alkoxy group, a $C_1$–$C_4$ alkylthio group, or a $C_1$–$C_4$ haloalkoxy group; l is 0; and m is 1 or 2.

Further preferred compounds are those wherein $R_1$ is a methyl group; $R^2$ and X combine together to form

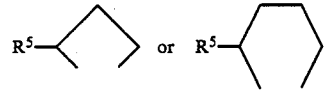

wherein $R^5$ is a hydrogen atom or a methyl group; $R^3$ is a hydrogen atom; $R^4$ is an n-propyl group, an isopropyl group, an n-butyl group, a t-butyl group, an n-pentyl group, a methoxy group, an ethoxy group, an n-propoxy group, a 2,2,2-trifluoroethoxy group, a 2,2,3,3,3-pentafluoropropoxy group or an n-propylthio group; l is 0; and m is 1.

The pyrazole derivative of the present invention represented by the formula (I) can be produced according to, for example, the following reaction formula:

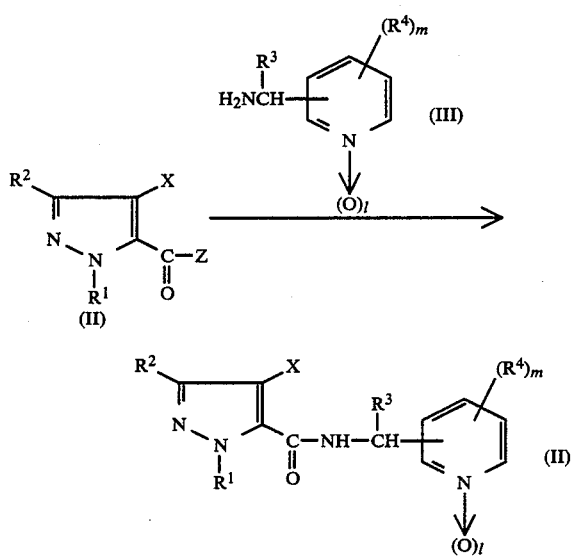

In the above reaction formula, $R^1$, $R^2$, $R^3$, $R^4$, X, l and m are the same as has been defined in the formula (I), and Z represents a chlorine atom, a bromine atom, a hydroxyl group, a methoxy group, an ethoxy group or a propoxy group.

In the case where Z represents a chlorine atom or a bromine atom in the formula (II), the pyrazole derivative of the formula (I) can be obtained by reacting the compound (II) with the compound (III) at 0° to 30° C., preferably 0° to 5° C. in a aromatic hydrocarbon such as benzene, toluene and xylene; a ketone such as acetone, methyl ethyl ketone and methyl isobutyl ketone; a halogenated hydrocarbon such as chloroform and methylene chloride; water; an ester such as methyl acetate and ethyl acetate; or a polar solvent such as tetrahydrofuran, acetonitrile, dioxane, N,N-dimethylformamide, N-methylpyrrolidone and dimethyl sulfoxide in the presence of a base.

As the base, sodium hydroxide, potassium hydroxide, sodium carbonate, potassium carbonate, pyridine or triethylamine, etc. may be mentioned.

In the case where Z represents a hydroxyl group, a methoxy group, an ethoxy group or a propoxy group in the formula (II), the pyrazole derivative of the formula (I) can be obtained by reacting the compound (II) with the compound (III) at 150° to 250° C., preferably 200° to 250° C. without using any solvent or using a solvent of a high boiling point such as N,N-dimethylformamide, N-methylpyrrolidone or dimethyl sulfoxide, etc.

The compound (II) can be produced by following the method described in, for example, Annalen der Chemie, Justus Liebig's, 536, 97 (1938), and the compound (III) can be produced by following the method described in, for example, Journal für Praktische Chemie, 146, 95 (1936).

Although the pyrazole derivative represented by the formula (I) has a significant control activity against eggs and larvae of insects of Coleoptera, Lepidoptera, Hemiptera, Orthoptera, Diptera, as well as eggs and larvae of Spider mite. As a matter of course, insects and mites against which the pyrazole derivative represented by the formula (I) shows a remarkable controlling activity are not limited to those exemplified below.

1. Hemiptera; Planthoppers such as *Sogatella frucifera, Nilaparvata lugens, Laodelphax striatellus*, etc.; leafhoppers such as *Nephotettix cincticeps, Cicadella viridis*, etc. and Aphis such as *Myzus persicae*, etc.

2. Lepidoptera; *Spodoptera litura, Chilo suppressalis, Cnaphalocrosis medinalis*, etc.

3. Coleoptera; *Callosobruchus chinensis*, etc.

4. Diptera; *Musca domestica, Aedes aegypti, Culex pipiens molestus*, etc.

5. Spider mite; *Tetranychus urticae, Tetranychus cinnabarinus, Panonychus citri*, etc.

The pyrazole derivative according to the present invention has not only insecticidal activity and miticidal activity, but also a remarkable fungicidal activity atainst pathogens such as *Pyricularia oryzae, Phytophthora, Peronospora*, etc.

In the case of using the pyrazole derivative represented by the formula (I) according to the present invention as an insecticide miticide or fungicide, it may be used alone or usually formulated into a composition such as emulsifiable concentrate, dust, wettable powder, solution, etc. together with adjuvants in the same manner as conventional agricultural chemicals and then used without or after dilution. The adjuvants are those used ordinarily for the formulation of the insecticides. For instance, there can be mentioned solid carrier such as talc, kaolin, diatomaceous earth, clay and starch; water; hydrocarbons such as cyclohexane, benzene, xylene and toluene; halogenated hydrocarbons such as chlorobenzene; ethers; amides such as dimethylformamide; ketones; alcohols; nitriles such as acetonitrile, as well as other known surface active agents such as emulsifiers and dispersing agents.

If desired, it is also possible to use in admixture or combination with other insecticides, miticides, fungicides, insect growth controlling agent, plant growth controlling agent, etc. Although the concentration of the active ingredient in the formulated insecticidal, miticidal or fungicidal composition has no particular restrictions, it is usually contained from 0.5 to 20 % by weight, preferably, from 1 to 10 % by weight in dust; from 1 to 90 % by weight, preferably, from 10 to 80 % by weight in wettable powder; and from 1 to 90 % by weight, preferably, from 10 to 40 % by weight in emulsifiable concentrate.

In the case of using the pyrazole derivative represented by the formula (I) as the insecticide, miticide or fungicide, it is usually used after dilution within the range of concentration of the active ingredient from 5 to 1000 ppm, preferably, from 10 to 500 ppm.

The present invention will be explained more specifically referring to the following preparation examples, formulation examples and test examples for the compound according to the present invention, but it should be understood that the present invention is not restricted only to the following examples.

EXAMPLE 1

Preparation of N-[(6-t-butyl-3-pyridyl)methyl]-4-chloro-1,3-dimethyl-5-pyrazolecarboxamide.

A mixture of 1.74 g of 4-chloro-1,3-dimethylpyrazole-5-carboxylic acid and 2.38 g of thionyl chloride was refluxed for one hour. After distilling off thionyl chloride under a reduced pressure, the residue was dissolved in 20 ml of toluene. The thus formed solution was dropped into 25 ml of a toluene solution of 1.62 g of 5-aminomethyl-2-t-butylpyridine and 1.21 g of triethylamine at a temperature of 0° ~ 10° C.

Thereafter, the thus formed mixture was stirred for 2 hours, poured into iced water, and then extracted with toluene. After washing the toluene layer with an aqueous sodium carbonate, water and saturated saline solution in the order, the toluene layer was dried over anhydrous sodium sulfate and concentrated under a reduced pressure. The residue was purified by silica gel columnchromatography to obtain 2.70 g of the compound (No.3) listed in Table 1.

The NMR and IR spectra of the thus obtained compound were as follows:

$^1$H-NMR(CDCl$_3$) δ ppm; 1.35(s,9H), 2.2(s,3H), 4.1(s,3H), 4.55
(d,2H), 6.95(b,1H), 7.25(d,1H), 7.6(d-d, 1H), 8.5(d,1H)
IR(KRb) cm$^{-1}$; 3440, 3380, 2960, 1655, 1525, 1505, 1280, 1140, 1090

EXAMPLE 2

Preparation of N-[(6-n-butyl-3-pyridyl)methyl]-chloro-3-ethyl-1-methyl-5-pyrazolecarboxamide.

A mixture of 2.17 g of ethyl 4-chloro-3-ethyl-1-methylpyrazole-5-carboxylate and 3.24 g of 5-aminomethyl-2-n-butylpyridine was heated at 200° C. for 4 hours under stirring. After cooling to room temperature, the reaction mixture was purified by silica gel columnchromatography to obtain 2.06 g of the compound (NO. 15) listed in Table 1.

The NMR and IR spectra of the thus obtained compound were as follows:

$^1$H-NMR(CDCl$_3$) δ ppm; 0.94(t, 3H), 1.15–1.90(m, 4H), 1.25 (t, 3H), 2.63(q, 2H), 2.81(t, 2H), 4.15(s, 3H), 4.63(d, 2H), 7.08(b, 1H), 7.17(d, 1H), 7.63(d-d, 1H), 8.56(d, 1H)

IR(KBr) cm$^{-1}$; 3270, 2955, 1640, 1555, 1485, 1460, 1400, 1290, 1090, 1035

EXAMPLE 3

Preparation of N-[(6-t-butyl-3-pyridyl)methyl]-methyl-4,5,6,7-tetrahydro-2H-indazole-3-carboxamide A mixture of 1.8 g of 2-methyl-4,5,6,7-tetrahydro-2H-indazole-3-carboxylic acid and 11.7 g of thionyl chloride was refluxed for one hour. After distilling off thionyl chloride under a reduced pressure, the residue was dissolved in 20 ml of toluene. The thus formed solution was dropped into 25 ml of a toluene solution of 1.6 g of 5-aminomethyl-2-t-butylpyridine and 1.2 g of triethylamine at 0° ~° C. Thereafter, the thus formed mixture was stirred for 2 hours, poured into iced water, and then extracted with toluene. After washing with an aqueous sodium carbonate, water and saturated saline solution, the toluene layer was dried over anhydrous sodium sulfate, and concentrated under a reduced pressure.

The residue was purified by silica gel columnchromatography to obtain 2.3 g of the compound (No. 72) listed in Table 1.

The NMR and IR spectra of the thus obtained compound were as follows:

$^1$H-NMR(CDCl$_3$) δ ppm; 1.35 (s, 9H), 1.8(m, 4H), 2.6(m, 4H), 4.05(s, 3H), 4.5(d, 2H), 5.85(b-s, 1H), 7.25(d, 1H), 7.55(dd, 1H), 8.45(d, 1H)

IR(KBr)cm$^{-1}$; 3340, 2950, 1640, 1540, 1520, 1285, 970, 840

EXAMPLE 4

Preparation of N-[(6-n-butyl-3-pyridyl)methyl]-2-methyl-cyclopenta[1,2-C]-3-pyrazolecarboxamide A mixture of 2 g of ethyl 2-methyl-cyclopenta[1,2-C]-3pyrazolecarboxylate and 3.3 g of 5-aminomethyl-2-n-butylpyridine was heated at 200° C. for 4 hours under stirring. After cooling to room temperature, the reaction mixture was purified by silica gel columnchromatography to obtain 2.6 g of the compound (No. 50) listed in Table 1.

The NMR and IR spectra of the thus obtained compound were as follows:

$^1$H-NMR(CCl$_4$) δ ppm; 0.93(t, 3H), 1.15 δ1.92(m, 4H), 2.3 δ2.92(m, 8H), 4.18(s, 3H), 4.58(d, 2H), 6.1(b-s, 1H), 7.18(d, 1H), 7.62(d-d, 1H), 8.53(d, 1H).

IR(KBr) cm$^{-1}$; 3270, 2950, 1640, 1560, 1530, 1370, 1295.

EXAMPLE 5

Preparation of N-[[6-(4-chlorophenoxy)-3-pyridyl]methyl]-2,6-dimethylcyclopenta[1,2-C]-3-pyrazolecarboxamide A mixture of 1.66 g of 2,6-dimethylcyclopenta[1,2-C]-3-pyrazolecarboxylic acid and 3.6 g of thionyl chloride was refluxed for one hour. After distilling off thionyl chloride under a reduced pressure, the residue was dissolved in 20 ml of toluene. The thus obtained solution was dropped in 25 ml of a toluene solution of 2.36 g of 5-aminomethyl-2-(4-chlorophenoxy)-pyridine and 1.21 g of triethylamine at 0° ~5° C.

Thereafter, the thus formed mixture was stirred for 2 hours and poured into iced water. After washing with water and saturated saline solution, the organic layer was dried over anhydrous sodium sulfate and then the solvent was distilled off under a reduced pressure. The residue was purified by silica gel columnchromatography to obtain 3.14 g of the compound (No. 98) listed in Table 1.

The NMR and IR spectra of the thus obtained compound were as follows:

$^1$H-NMR(CDCl$_3$) δ ppm; 1.26(d, 3H), 1.8 δ2.3(m, 1H), 2.5 δ 2.85
(m, 3H), 3.0~3.3(m, 1H), 4.17(s, 3H),
4.56(d, 2H), 6.05(bs, 1H), 6.93(d, 1H),
7.08(d, 2H), 7.39(d, 2H), 7.75(d-d, 1H), 8.16(d, 1H)
IR(KBr) cm$^{-1}$; 3300, 2950, 1640, 1555, 1530, 1475, 1285, 1245.

EXAMPLE 6

Following the methods in Examples 1 to 5, the compounds listed in Table 1 were respectively obtained.

TABLE 1
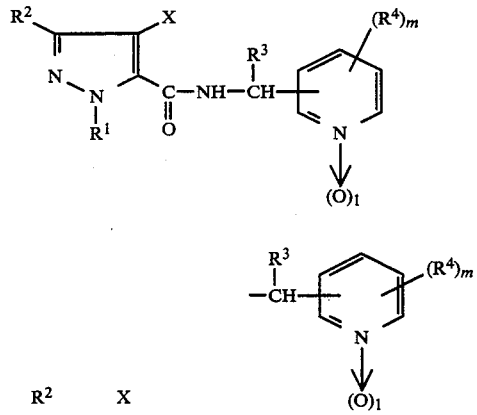
(I)
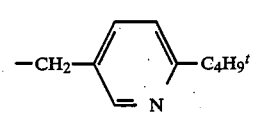
| Compound No. | R¹ | R² | X | | $n_D$ (refractive index) Melting point (°C.) |
|---|---|---|---|---|---|
| 1 | CH₃ | H | Cl | 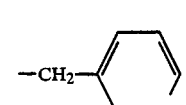 | $n_D^{25}$ 1.5553 |
| 2 | " | CH₃ | " | 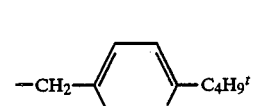 | 96–97 |
| 3 | " | " | " | 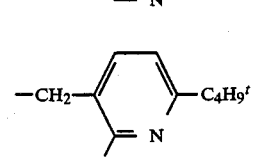 | 65–68 |
| 4 | " | " | " | 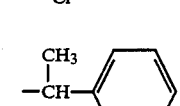 | 106–107 |
| 5 | CH₃ | CH₃ | Br | 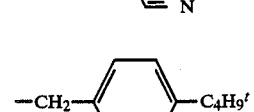 | 77–79 |
| 6 | " | C₂H₅ | H | 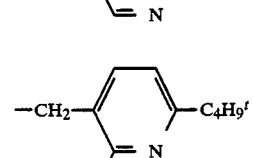 | 78–79 |
| 7 | " | " | " | 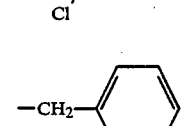 | amorphous* |
| 8 | " | " | Cl | —CH₂—(2-pyridyl) | 79–80 |
| 9 | " | " | " | 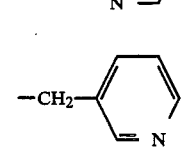 | 72–74 |

TABLE 1-continued $$\text{(I)}$$

Structure: Pyrazole with $R^2$ at 3-position, $X$ at 4-position, $R^1$ on N, and a C(=O)NH-CH($R^3$)-[pyridine N-oxide with $(R^4)_m$] group.

Substituent group: $-CH(R^3)-$[pyridine with $(R^4)_m$, N-oxide $(O)_1$]

| Compound No. | $R^1$ | $R^2$ | X | Substituent | $n_D$ (refractive index) / Melting point (°C.) |
|---|---|---|---|---|---|
| 10 | " | " | " | $-CH_2-$(4-pyridyl) | 75–77 |
| 11 | $CH_3$ | $C_2H_5$ | Cl | $-CH_2-$(6-Br-pyridyl) | 119–120 |
| 12 | " | " | " | $-CH_2-$(2-Cl-pyridyl) | 124–126 |
| 13 | " | " | " | $-CH_2-$(6-$C_3H_7^n$-pyridyl) | 77–79 |
| 14 | " | " | " | $-CH_2-$(6-$C_3H_7^i$-pyridyl) | 72–74 |
| 15 | " | " | " | $-CH_2-$(6-$C_4H_9^n$-pyridyl) | 87–88 |
| 16 | " | " | " | $-CH_2-$(6-$C_4H_9^i$-pyridyl) | 94–95 |
| 17 | " | " | " | $-CH_2-$(6-$C_4H_9^t$-pyridyl) | $n_D^{25}$ 1.5458 |
| 18 | $CH_3$ | $C_2H_5$ | Cl | $-CH_2-$(6-$C_5H_{11}^n$-pyridyl) | 65–66 |
| 19 | " | " | " | $-CH_2-$(6-$CH_2C(CH_3)_3$-pyridyl) | $n_D^{25}$ 1.5340 |

TABLE 1-continued
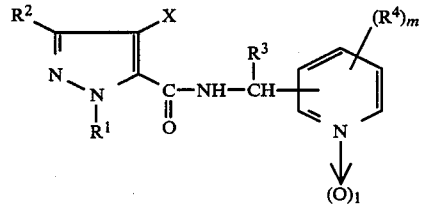
(I)
| Compound No. | R¹ | R² | X | [substituent] | $n_D$ (refractive index) Melting point (°C.) |
|---|---|---|---|---|---|
| 20 | " | " | " | —CH₂— pyridine —OC₃H₇ⁿ | 99–100 |
| 21 | " | " | " | —CH₂— pyridine —OC₃H₇ⁱ | 94–95 |
| 22 | " | " | " | —CH₂— pyridine —OC₄H₉ⁿ | 79–80 |
| 23 | " | " | " | —CH₂— pyridine (4-CH₃, 6-CH₃) | 153–155 |
| 24 | " | " | " | —CH₂— pyridine (4-CH₃, 6-C₄H₉ⁿ) | 90–92 |
| 25 | CH₃ | C₂H₅ | Cl | —CH₂— tetrahydroquinoline-CH₃ | 106–108 |
| 26 | " | " | " | —CH₂— pyridine (2-Cl, 6-C₃H₇ⁿ) | 73–75 |
| 27 | " | " | " | —CH₂— pyridine (2-Cl, 6-C₃H₇ⁱ) | 46–48 |

TABLE 1-continued

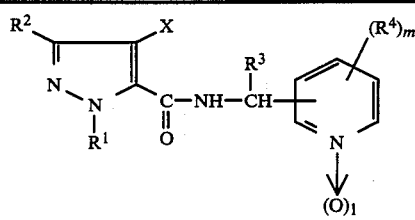

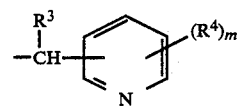

| Compound No. | $R^1$ | $R^2$ | X | | $n_D$ (refractive index) Melting point (°C.) |
|---|---|---|---|---|---|
| 28 | " | " | " | -CH₂-[pyridine with Cl, $C_4H_9^n$] | 83–84 |
| 29 | " | " | " | -CH₂-[pyridine with F, $C_4H_9^n$] | 111–112 |
| 30 | " | " | " | -CH₂-[pyridine with Cl, $C_4H_9^i$] | 97–98 |
| 31 | " | " | " | -CH₂-[pyridine with Cl, $C_4H_9^t$] | $n_D^{25}$ 1.5412 |
| 32 | $CH_3$ | $C_2H_5$ | Cl | -CH₂-[pyridine with Cl, $C_5H_{11}^n$] | 74–76 |
| 33 | " | " | " | -CH₂-[pyridine with Cl, $CH_2C(CH_3)_3$] | 73–75 |
| 34 | " | " | " | -CH₂-[pyridine with Cl, phenyl-$C_4H_9^t$] | 108–110 |
| 35 | " | " | " | -CH₂-[pyridine with $CH_3S$, $C_4H_9^t$] | $n_D^{25}$ 1.5633 |

TABLE 1-continued
(I)
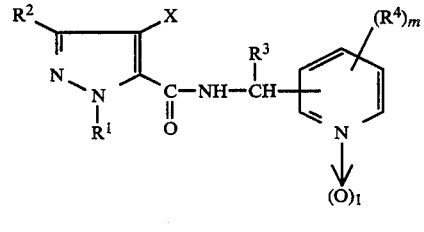
| Compound No. | R¹ | R² | X | [substituent] | $n_D$ (refractive index) Melting point (°C.) |
|---|---|---|---|---|---|
| 36 | " | " | " | 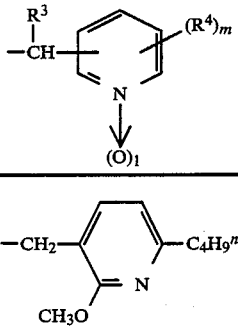 | 59–60 |
| 37 | " | " | " | 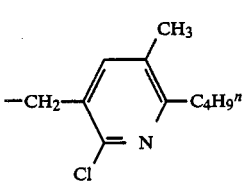 | 111–112 |
| 38 | " | " | " | 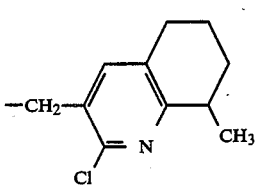 | 121–123 |
| 39 | $CH_3$ | 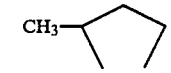 | | 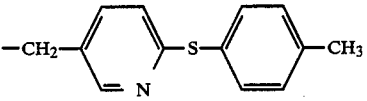 | 155–156 |
| 40 | " | $C_2H_5$ | Br | 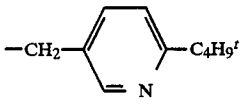 | 88–89 |
| 41 | " | " | " | 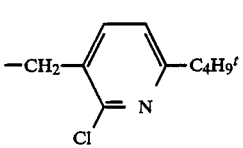 | 92–94 |
| 42 | " | " | $CH_3$ | 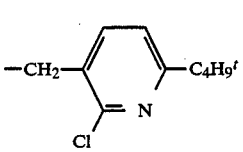 | $n_D^{25}$ 1.5367 |
| 43 | $C_2H_5$ | $C_2H_5$ | Cl | 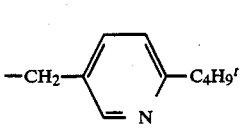 | 65–66 |

TABLE 1-continued
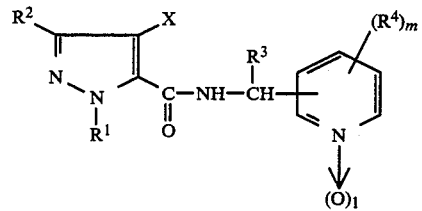
(I)
| Compound No. | R¹ | R² | X | (structure) | $n_D$ (refractive index) Melting point (°C.) |
|---|---|---|---|---|---|
| 46 | CH₃ |  | | 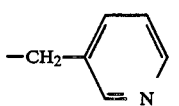 | 121–122 |
| 47 | " | " | | 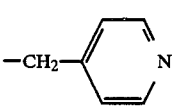 | 125–126 |
| 48 | " | " | | 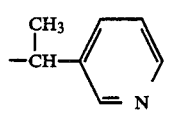 | 114–115 |
| 49 | " | " | | 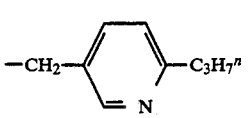 | 113–115 |
| 50 | " | " | | 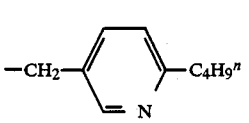 | 93–95 |
| 51 | " | " | | 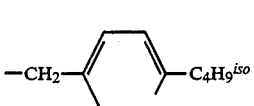 | 90–92 |
| 52 | " | " | | 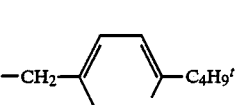 | 121–124 |
| 53 | CH₃ |  | | 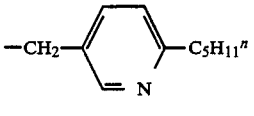 | 80–82 |
| 54 | " | " | | 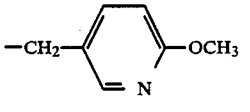 | 121–123 |
| 55 | " | " | | 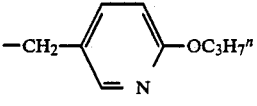 | 120–121 |

TABLE 1-continued $$\text{(I)}$$

Structure (I): pyrazole ring with R² at 3-position, X at 4-position, R¹ on N1, and a -C(O)-NH-CH(R³)- group at 5-position connecting to a pyridine ring bearing $(R^4)_m$ substituents, with optional N-oxide $(O)_l$.

Substituent group shown: $-CH(R^3)-$ pyridine with $(R^4)_m$ and $(O)_l$.

| Compound No. | R¹ | R² | X | [pyridyl group] | $n_D$ (refractive index) Melting point (°C.) |
|---|---|---|---|---|---|
| 56 | " | " | | $-CH_2-$pyridine-$OCH_2CF_3$ | 140–142 |
| 57 | " | " | | $-CH_2-$pyridine-$SCH_3$ | 164–165 |
| 58 | " | " | | $-CH_2-$pyridine-$SC_3H_7{}^n$ | 107–109 |
| 59 | " | " | | $-CH_2-$pyridine-$Br$ | 136–138 |
| 60 | $CH_3$ | cyclopentyl | | $-CH_2-$pyridine-$C_4H_9{}^n$, N-oxide | $n_D{}^{25}$ 1.5180 |
| 61 | " | " | | $-CH_2-$pyridine-$C_4H_9{}^t$, N-oxide | 178–180 |
| 62 | " | " | | $-CH_2-$pyridine with $CH_3$ and $CH_3$ | 145–147 |
| 63 | " | " | | $-CH_2-$pyridine with $CH_3$ and $C_4H_9{}^n$ | 113–114 |

TABLE 1-continued

Structure (I):

$$R^2\text{-pyrazole-}C(=O)\text{NH-CH}(R^3)\text{-pyridine}(R^4)_m\text{-}(O)_1$$

with $R^1$ on pyrazole N.

Side chain: $-CH(R^3)-$pyridine$(R^4)_m$-$(O)_1$

| Compound No. | $R^1$ | $R^2$ | X | pyridine substituent | $n_D$ (refractive index) Melting point (°C.) |
|---|---|---|---|---|---|
| 64 | " | " | | $-CH_2-$pyridine($C_4H_9^n$, $OCH_3$) | 92–94 |
| 65 | " | " | | $-CH_2-$pyridine($C_4H_9^t$, $SCH_3$) | 102–103 |
| 66 | " | " | | $-CH_2-$pyridine($C_4H_9^t$, $Cl$) | 135–137 |
| 67 | $C_2H_5$ | cyclopentyl | | $-CH_2-$pyridine($C_4H_9^t$) | 92–94 |
| 68 | " | " | | $-CH_2-$pyridine($C_4H_9^t$, $Cl$) | 96–98 |
| 69 | $C_4H_9t$ | " | | $-CH_2-$pyridine($C_4H_9^t$) | 152–153 |
| 70 | $CH_3$ | sec-pentyl ($CH_3$CH-) | | $-CH_2-$pyridine($C_4H_9^n$) | 87–89 |
| 71 | " | " | | $-CH_2-$pyridine($C_4H_9^t$) | 98–100 |
| 72 | " | cyclohexyl | | " | 128–130 |

TABLE 1-continued
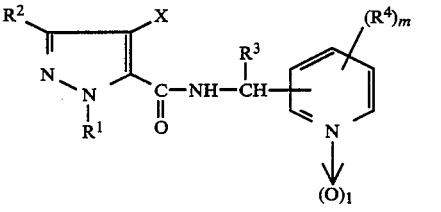
(I)
| Compound No. | R¹ | R² | X | (structure) | $n_D$ (refractive index) Melting point (°C.) |
|---|---|---|---|---|---|
| 73 | " | " | | 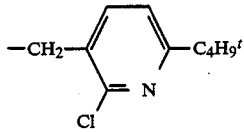 | 147–149 |
| 74 | CH₃ | 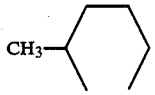 | | 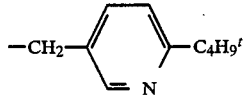 | 109–111 |
| 75 | " |  | | 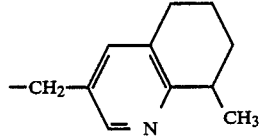 | 140–142 |
| 76 | 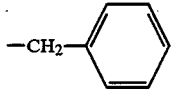 | " | | 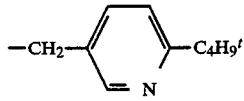 | 119–121 |
| 77 | CH₃ | 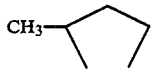 | | 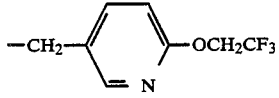 | 137–139 |
| 78 | " |  | | 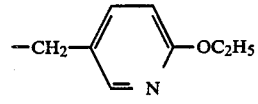 | 140–141 |
| 79 | " | " | | 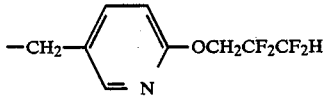 | 122–123 |
| 80 | " | " | | 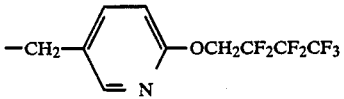 | 117–118 |
| 81 | CH₃ |  | | 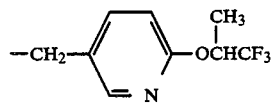 | 116–118 |

TABLE 1-continued $$\text{(I)}$$

Structure (I): pyrazole with $R^2$ at 3-position, X at 4-position, $R^1$ on N1, carboxamide at 5-position linked to –NH–CH($R^3$)– attached to pyridine ring bearing $(R^4)_m$ substituents, with pyridine N-oxide $(O)_l$.

| Compound No. | $R^1$ | $R^2$ | X | $-CH(R^3)-$pyridine-$(R^4)_m$-$(O)_l$ group | $n_D$ (refractive index) Melting point (°C.) |
|---|---|---|---|---|---|
| 82 | " | " |  | $-CH_2-$pyridyl-$OCH_2CF_2CF_3$ | 136–137 |
| 83 | " | " |  | $-CH_2-$pyridyl-$C_3H_7^i$ | 110–112 |
| 84 | " | " |  | $-CH_2-$pyridyl-$C_4H_9^s$ | 58–60 |
| 85 | " | $CH_3\text{-}CH(CH_3)CH_2CH_3$ (sec-butyl) |  | $-CH_2-$pyridyl-$OCH_2CF_2CF_3$ | 111–112 |
| 86 | " | " |  | $-CH_2-$pyridyl-$OCH_2CH_2CH_2CF_3$ | 112–114 |
| 87 | " | " |  | $-CH_2-$pyridyl-$OCH_2CF_2CF_2CF_3$ | 107–108 |
| 88 | $CH_3$ | H | H | $-CH_2-$pyridyl-$C_4H_9^t$ | 86–88 |
| 89 | " | $C_2H_5$ | Cl | $-CH_2-$pyridyl-$OCH_2CF_2CF_2H$ | 87–89 |
| 90 | " | " | " | $-CH_2-$pyridyl-$OCH_2CF_2CF_2CF_3$ | 63–65 |
| 91 | " | " | " | $-CH_2-$pyridyl-$OCH(CH_3)CF_3$ | 76–79 |

TABLE 1-continued

Structure (I):

R² and X substituents on a pyrazole ring with N-R¹, connected via C(=O)-NH-CH(R³)- to a pyridine ring bearing (R⁴)ₘ and N→(O)ₗ.

The column shows: -CH(R³)- attached to pyridine with (R⁴)ₘ and N→(O)ₗ.

| Compound No. | R¹ | R² | X | (substituent group) | n_D (refractive index) Melting point (°C.) |
|---|---|---|---|---|---|
| 92 | " | " | " | -CH₂-(pyridyl)-OCH₂CF₂CF₃ | 84–85 |
| 93 | " | " | " | -CH₂-(pyridyl)-OCH₂CH₂CH₂CF₃ | 92–94 |
| 94 | " | " | " | -CH₂-(pyridyl)-O-phenyl | 113–114 |
| 95 | CH₃ | C₂H₅ | Cl | -CH₂-(pyridyl)-O-(4-Cl-phenyl) | 146–148 |
| 96 | " | CH₃ | Br | -CH₂-(pyridyl)-O-(4-Cl-phenyl) | 153–154 |
| 97 | " | " | CH₃ | " | 149–150 |
| 98 | " | CH₃-CH(cyclobutyl) | | " | 127–128 |
| 99 | " | cyclohexyl | | " | 144–145 |
| 100 | " | C₂H₅ | Cl | -CH₂-(pyridyl)-O-(4-CF₃-phenyl) | 136–137 |
| 101 | " | CH₃-CH(cyclobutyl) | | " | 132–133 |
| 102 | CH₃ | C₂H₅ | Cl | -CH₂-(pyridyl)-O-(4-OCH₃-phenyl) | 103–104 |
| 103 | " | CH₃-CH(cyclobutyl) | | " | 143–144 |

TABLE 1-continued

| Compound No. | R¹ | R² | X | | $n_D$ (refractive index) Melting point (°C.) |
|---|---|---|---|---|---|
| 104 | " | | | " | 157–158 |
| 105 | " | 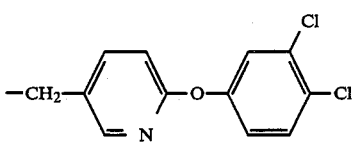 | | 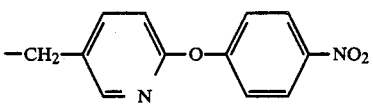 | 137–139 |
| 106 | " | " | | 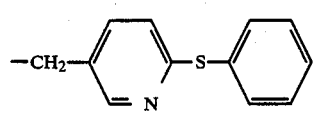 | 159–160 |
| 107 | " | " | | 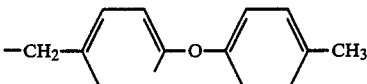 | 78–80 |
| 108 | " | $C_2H_5$ | Cl | " | 91–92 |
| 109 | $CH_3$ | $C_2H_5$ | Cl | 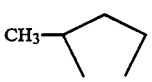 | 124–125 |
| 110 | " | CH₃—⟨cyclopentyl⟩ | | " | 150–151 |

Note:
*The NMR and IR spectra of the compound No. 7 of Table 1 were as follows:
¹H-NMR (CCl₄) δ ppm; 1.20 (t, 3H), 1.35 (s, 9H), 2.54 (q, sH), 4.05 (s, 3H), 4.54 (d, 2H), 6.21 (s, 1H), 6.43 (b, 1H), 7.2 (d, 1H), 7.72 (d, 1H)
IR(KBr) cm⁻¹; 3320, 2960, 1655, 1590, 1510, 1435, 1370, 1327, 1270, 1140, 1070

Formulation Examples of the compound of the present invention are shown below. The terms "parts" and "%" represent "parts by weight" and "% by weight", respectively.

FORMULATION EXAMPLE 1

Wettable powder

A wettable powder containing 40 % of an active ingredient was prepared by uniformly mixing and pulverizing 20 parts of each of the pyrazole derivatives of the present invention shown in Table 1, 20 parts of Carplex #80 (trade name, produced by Shionogi Seiyaku Co.), 55 parts of N,N Kaolin Clay (trade name, produced by Tsuchiya Kaolin Co.) and 5 parts of higher alcohol sulfuric acid ester type surfactant Sorpol 8070 (trade name, Toho Kagaku Co.).

FORMULATION EXAMPLE 2

Dust

A dust containing 2 % of an active ingredient was prepared by uniformly mixing and pulverizing 2 parts of each of the pyrazole compounds of the present invention shown in Table 1, 93 parts of clay (produced by Nippon Talc Co.) and 5 parts of white carbon.

FORMULATION EXAMPLE 3

Emulsifiable Concentrate

In a mixed solvent containing 35 parts of xylene and 30 parts of dimethylformamide, was dissolved 20 parts of each of the pyrazole derivatives of the present invention shown in Table 1. Then, 15 parts of polyoxyethylene type surfactant Sorpol 3005X (trade name, produced by Toho Kagaku Co.) was added to the obtained solution to obtain an emulsifiable concentrate containing 20 % of an active ingredient.

FORMULATION EXAMPLE 4

Flowable Agent

A stable flowable agent containing 30 % of an active ingredients was prepared by mixing and dispersing 30 parts of each of the pyrazole derivative according to the present invention shown in Table 1 and a previously prepared mixture of 8 parts of ethylene glycol, 5 parts of Sorpol AC 3032 (trade name, manufactured by Toho Kagaku Co.) and 0.1 part of xanthene gum into 56.9 parts of water, and then pulverizing the slurrylike mixture in the wet process in a DYNO-MILL (manufactured by Shinmaru Enterprises Co.).

TEST EXAMPLE 1

Effect against adult *Tetranychus urticae*

Then female adult *Tetranychus urticae* were put on a leaf disc (2 cm diameter) of a kidney bean leaf. Then, 5 ml of a solution, prepared by diluting each of insecticidal and miticidal compositions of the present invention formulated in accordance with the preparation of Formulation Example 1 with water to a predetermined concentration, was scattered by using a rotary type scattering tower (manufactured by Mizuho Rika Co.). Test was repeated twice for each concentration.

Twenty four hours after the treatment, the number of live and dead larvae were counted and the miticidal activity (%) was determined by the following equation.

$$\text{Miticidal Activity (\%)} = \frac{\text{Number of dead larvae}}{\text{Number of treated larvae}} \times 100$$

The results are shown in Table 2.

TEST EXAMPLE 2

Effect against eggs of *Tetranychus urticae*

Five female adult *Tetranychus urticae* were put on a leaf disc (2 cm diameter) of a kidney bean leaf. The mites were allowed to oviposit on the leaf disc for 20 hours after putting and then the adult females mites were removed. Then, 5 ml of a solution, prepared by diluting each of insecticidal and miticidal compositions of the present invention formulated in accordance with the preparation of Formulation Example 1 with water to a predetermined concentration, was scattered by using a rotary type scattering tower (manufactured by Mizuho Rika Co.). Test was repeated twice for each concentration.

The number of unhatched eggs and the number of hatched larvae were counted 5 days after the treatment to determine the ovicidal activity (%) by the following equation Ovicidal Activity (%) =

$$\frac{\text{Number of unhatched eggs}}{\text{Number of unhatched eggs} + \text{Number of hatched eggs}}$$

The results are shown in Table 2.

TABLE 2

| Compound No. | Concentration (ppm) | Miticidal Activity (%) | Ovicidal Activity (%) |
|---|---|---|---|
| 1 | 500 | 100 | 100 |
| 3 | " | " | " |
| 4 | " | " | " |
| 6 | 500 | " | " |
|   | 50 | " | " |
| 7 | 500 | " | " |
| 9 | " | " | " |
| 13 | " | " | " |
| 14 | " | " | " |
| 15 | " | " | " |
| 16 | " | " | " |
| 17 | " | " | " |
| 18 | " | " | " |
| 19 | " | " | " |
| 20 | " | " | " |
| 21 | " | " | " |
| 22 | " | " | " |
| 24 | " | " | " |
| 25 | " | " | " |
| 28 | " | " | " |
| 29 | " | " | " |
| 31 | " | " | " |
| 35 | " | " | " |
| 36 | " | " | " |
| 40 | " | " | " |
| 49 | " | " | " |
| 50 | " | " | " |
| 51 | " | " | " |
| 52 | " | " | " |
| 53 | " | " | " |
| 55 | " | " | " |
| 56 | 500 | " | " |
|   | 50 | " | " |
| 58 | 500 | " | " |
| 60 | " | " | " |
| 61 | " | " | " |
| 63 | " | " | " |
| 64 | " | " | " |
| 66 | " | " | " |
| 70 | " | " | " |
| 71 | " | " | " |
| 72 | " | " | " |
| 74 | " | " | " |
| 77 | 500 | " | " |
|   | 50 | " | " |
| 79 | 500 | " | " |
| 80 | " | " | " |
| 81 | " | " | " |
| 82 | " | " | " |
| 83 | " | " | " |
| 84 | " | " | " |
| 85 | 500 | " | " |
|   | 50 | " | " |
| 86 | 500 | " | " |
| 87 | " | " | " |
| 88 | " | " | " |
| 89 | " | " | " |
| 90 | " | " | " |
| 91 | " | " | " |
| 92 | " | " | " |
| 93 | " | " | " |
| 98 | " | " | " |
| 101 | 500 | " | " |
|   | 50 | " | " |

TEST EXAMPLE 3

Effect against larvae of *Nilaparvata lugens*

Germinated seedlings of rice plant were set to a glass cylinder (3 cm diameter, 17 cm length) and five larvae of fourth instar of *Nilaparvata lugens* were put to them.

Then, each of the insecticidal and miticidal compositions according to the present invention formulated in accordance with the preparation of Formulation Example 3 was diluted with water and scattered by 0.5 ml using a scattering tower (manufactured by Mizuho Rika Co.). Test was repeated four times for each concentration. Twenty-four hours after the treatment, the number of dead larvae was counted to determine the mortality (%). The results are shown in Table 3.

$$\text{Mortality (\%)} = \frac{\text{Number of dead larvae}}{\text{Number of treated larvae}} \times 100$$

TABLE 3

| Compound No. | Concentration (ppm) | Mortality (%) |
|---|---|---|
| 3 | 500 | 100 |
| 6 | " | " |
| 13 | " | " |
| 14 | " | " |
| 15 | " | " |
| 17 | " | " |
| 20 | " | " |
| 21 | " | " |
| 22 | " | " |
| 24 | " | " |
| 26 | " | " |
| 29 | " | " |
| 36 | " | " |
| 40 | " | " |
| 50 | " | " |
| 53 | " | " |
| 55 | " | " |
| 56 | " | " |
| 58 | " | " |
| 64 | " | " |
| 70 | " | " |
| 71 | " | " |
| 72 | " | " |
| 74 | " | " |
| 78 | " | " |
| 79 | " | " |
| 80 | " | " |
| 81 | " | " |
| 82 | 500 | " |
|    | 50  | " |
| 84 | 500 | " |
| 85 | 500 | " |
|    | 50  | " |
| 86 | 500 | " |
| 87 | " | " |
| 88 | " | " |
| 89 | " | " |
| 90 | " | " |
| 91 | " | " |
| 92 | " | " |
| 93 | " | " |
| 95 | " | " |
| 96 | " | " |
| 97 | " | " |
| 98 | " | " |
| 99 | " | " |
| 100 | 500 | " |
|     | 50  | " |
| 101 | 500 | " | after immersion and placed in a plastic cup (7 cm diameter), to which five larvae of third instar of *Plutella xylostella* were put. Test was repeated twice for each concentration.

Four days after putting, the number of dead larvae was counted to determine the mortality (%).

The results are shown in Table 4.

TABLE 4

| Compound No. | Concentration (ppm) | Mortality (%) |
|---|---|---|
| 3 | 500 | 100 |
| 6 | " | " |
| 7 | " | " |
| 13 | " | " |
| 14 | " | " |
| 15 | " | " |
| 16 | " | " |
| 17 | " | " |
| 18 | " | " |
| 19 | " | " |
| 20 | " | " |
| 21 | " | " |
| 22 | " | " |
| 24 | " | " |
| 26 | " | " |
| 29 | " | " |
| 40 | " | " |
| 41 | " | " |
| 50 | " | " |
| 53 | " | " |
| 55 | " | " |
| 56 | " | " |
| 58 | " | " |
| 64 | " | " |
| 70 | " | " |
| 71 | " | " |
| 72 | " | " |
| 78 | " | " |
| 79 | " | " |
| 80 | " | " |
| 81 | " | " |
| 82 | " | " |
| 83 | " | " |
| 84 | " | " |
| 85 | " | " |
| 86 | " | " |
| 87 | 500 | " |
|    | 50  | " |
| 88 | 500 | " |
| 89 | " | " |
| 90 | " | " |
| 91 | 500 | " |
|    | 50  | " |
|    | 5   | " |
| 92 | 500 | " |
| 93 | " | " |
| 94 | " | " |
| 95 | " | " |
| 96 | " | " |
| 97 | " | " |
| 98 | " | " |
| 99 | " | " |
| 100 | " | " |
| 101 | " | " |

TEST EXAMPLE 4

Effect against larvae of *Plutella xylostella*

Slices of cabbage leaves (5×5 cm) were immersed for one minute in a water-diluted solution of each of the insecticidal and miticidal compositions of the present invention formulated in accordance with the preparation of Formulation Example 1. They were airdried

TEST EXAMPLE 5

Preventing effect against *Pyricularia oryzae* on rice plant

Each wettable powder prepared according to Formulation Example 1 and diluted with water to a predetermined concentration was applied, at a rate of 10 ml per pot, to stalks and leaves of 3 to 4 leaf stage of rice (variety: Nihonbare and Akinishiki) cultured 7 plants per a plastic pot (6 cm diameter). After air drying the liquid, a suspension of spores of *Pyricularia oryzae* cultured in Oat meal medium was inoculated by spraying. After keeping the inoculated rice plants in a humid chamber of 27° C. for 24 hours and then further leaving them in a water bath in a glass house for 3 days, the degree of morbidity was measured by observing spots appearing on the leaves and the prevention value was calculated from the following formula:

Prevention value (%) =

$$\frac{\text{(number of morbid spots per leaf in untreated plant)} - \text{(number of morbid spots per leaf in treated plant)}}{\text{(number of morbid spots per leaf in untreated plant)}} \times 100$$

The results are shown in Table 5.

TABLE 5

| Compound No. | Concentration (ppm) | Prevention Value (%) |
|---|---|---|
| 46 | 500 | 98 |
| 49 | " | 100 |
| 50 | " | 100 |
| 52 | " | 100 |
| 53 | " | 100 |
| 54 | " | 100 |
| 55 | " | 100 |
| 56 | " | 100 |
| 58 | " | 100 |
| 62 | " | 81 |
| 64 | " | 100 |
| 65 | " | 85 |
| 68 | " | 100 |
| 70 | " | 100 |
| 71 | " | 100 |
| 72 | " | 100 |
| 74 | " | 100 |
| 79 | " | 88 |
| 82 | " | 100 |
| 83 | " | 87 |
| 84 | " | 78 |
| 85 | " | 100 |

TEST EXAMPLE 6

Preventing effect against *Phytophthora infestans* on tomato

Each wettable powder prepared according to Formulation Example 1 and diluted with water to a predetermined concentration was applied at a rate of 10 ml per pot to stalks and leaves of 3 to 4 leaf stage of potato plants (variety: Red Cherry) cultured three plants per a plastic pot (6 cm diameter). After drying the applied liquid, a suspension of spores of *Phytophthora infestans* cultured on cut-leaves of tomato was inoculated by spraying. After keeping the inoculated tomato plants in a humid chamber of 20° C. for 24 hours and then further keeping them in a water bath in a glass house for 2 days, the mobid area on the tomato leaves was determined and classified into four morbidity indices of 0, 1, 3 and 5 as given below. Further, the prevention values were calculated from the following formula.

Morbidity index

0: Leaf had no sign of morbidity.

1: Leaf was morbid up to ⅓ of its total surface area.

3 Leaf was morbid through ⅓ to ⅔ of its total surface area.

5: Leaf was morbid over ⅔ of its total surface area.

Degree of morbidity (%) =

-continued $$\frac{0 \times n_0 + 1 \times n_1 + 3 \times n_3 + 5 \times n_5}{5(n_0 + n_1 + n_3 + n_5)} \times 100$$

where $n_0$, $n_1$, $n_3$ and $n_5$ respectively represent the number of leaves which show the morbidity index of 0, 1, 3 or 5 per one pot.

Prevention value (%) =

$$\frac{\text{(degree of morbidity in untreated plant)} - \text{(degree of morbidity in treated plant)}}{\text{(degree of morbidity in untreated plant)}} \times 100$$

The results are shown in Table 6.

TABLE 6

| Compound No. | Concentration (ppm) | Preventing Value (%) |
|---|---|---|
| 46 | 500 | 100 |
| 49 | " | 100 |
| 50 | 500 | 100 |
| 50 | 50 | 100 |
| 52 | 500 | 100 |
| 52 | 50 | 100 |
| 53 | 500 | 92 |
| 54 | " | 87 |
| 55 | " | 88 |
| 56 | " | 100 |
| 58 | " | 100 |
| 62 | " | 100 |
| 64 | " | 100 |
| 65 | " | 100 |
| 67 | " | 91 |
| 70 | " | 100 |
| 71 | " | 100 |
| 77 | " | 100 |
| 79 | " | 65 |
| 82 | " | 87 |
| 83 | " | 100 |
| 84 | " | 94 |
| 85 | " | 96 |

What is claimed is:

1. A pyrazole derivative represented by the following formula (I):

wherein $R^1$ represents a $C_1-C_4$ alkyl group or a benzyl group; $R^2$ represents a hydrogen atom or a $C_1-C_4$ alkyl group; X represents a hydrogen atom, a halogen atom or a $C_1-C_4$ alkyl group; $R^2$ may combine with X to form wherein $R^5$ represents a hydrogen atom or a $C_1-C_3$ alkyl group; $R^3$ represents a hydrogen atom or a $C_1-C_4$ alkyl group; $R^4$s independently represent a hydrogen atom, a halogen atom, a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group, a phenyl group, an alkyl-substituted phenyl group or

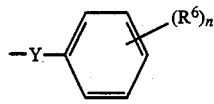

wherein Y represents an oxygen atom or a sulfur atom, $R^6$s independently represent a hydrogen atom, a $C_1$-$C_4$ alkyl group, a $C_1$-$C_4$ alkoxy group, a halogen atom, a nitro group, a cyano group or a trifluoromethyl group and n represents 1 or 2; l represents 0 or 1; and m represents 1, 2 or 3.

2. A pyrazole derivative according to claim 1, wherein $R^1$ represents a methyl group; $R^2$ represents a hydrogen atom or a $C_1$-$C_3$ alkyl group; X represents a hydrogen atom or a halogen atom; $R^2$ may combine with X to form

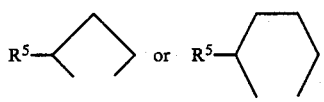

wherein $R^5$ represents a hydrogen atom or a methyl group; $R^3$ represents a hydrogen atom; $R^4$ represents a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group or

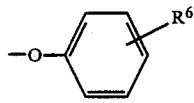

wherein $R^6$ represents a halogen atom or a trifluoromethyl group; l represents 0; and m represents 1 or 2.

3. An insecticidal and miticidal composition comprising as an active ingredient an insecticidally and miticidally effective amount of a pyrazole derivative represented by the following formula (I):

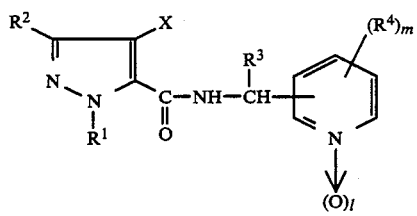

wherein $R^1$ represents a $C_1$-$C_4$ alkyl group or a benzyl group; $R^2$ represents a hydrogen atom or a $C_1$-$C_4$ alkyl group; X represents a hydrogen atom, a halogen atom or a $C_1$-$C_4$ alkyl group; $R^2$ may combine with X to form

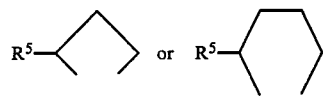

wherein $R^5$ represents a hydrogen atom or a $C_1$-$C_3$ alkyl group; $R^3$ represents a hydrogen atom or a $C_1$-$C_4$ alkyl group; $R^4$s independently represent a hydrogen atom, a halogen atom, a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group, a phenyl group, an alkyl-substituted phenyl group, or

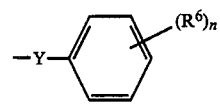

wherein Y represents an oxygen atom or a sulfur atom, $R^6$s independently represent a hydrogen atom, a $C_1$-$C_4$ alkyl group, a $C_1$-$C_4$ alkoxy group, a halogen atom, a nitro group, a cyano group or a trifluoromethyl group and n represents 1 or 2, l represents 0 or 1; and m represents 1, 2 or 3, and insecticidally and miticidally acceptable adjuvants.

4. The insecticidal and miticidal composition according to claim 3, wherein $R^1$ represents a methyl group; $R^2$ represents a hydrogen atom or a $C_1$-$C_3$ alkyl group; X represents a hydrogen atom or a halogen atom; $R^3$ represents a hydrogen atom; $R^4$ represents a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group or

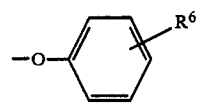

wherein $R^6$ represents a halogen atom or a trifluoromethyl group, l represents 0; and m represents 1 or 2.

5. The insecticidal and miticidal composition according to claim 3, wherein $R^1$ represents a methyl group; $R^2$ and X represent in combination

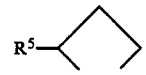

wherein $R^5$ represents a hydrogen atom or a methyl group; $R^3$ represents a hydrogen atom; $R^4$ represents a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group or

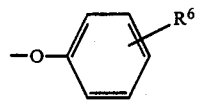

wherein $R^6$ represents a halogen atom or a trifluoromethyl group, l represents 0; and m represents 1 or 2.

6. A fungicidal composition comprising as an active ingredient a fungicidally effective amount of a pyrazole derivative represented by the following formula (I):

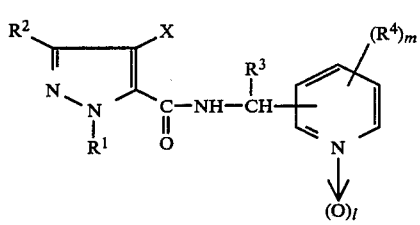

wherein $R^1$ represents a $C_1$-$C_4$ alkyl group or a benzyl group; $R^2$ represents a hydrogen atom or a $C_1$-$C_4$ alkyl group; X represents a hydrogen atom, a halogen atom or a $C_1$-$C_4$ alkyl group; $R^2$ may combine with X to form

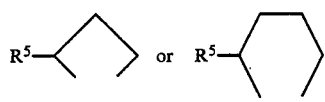

wherein $R^5$ represents a hydrogen atom or a $C_1$-$C_3$ alkyl group; $R^3$ represents a hydrogen atom or a $C_1$-$C_4$ alkyl group; $R^4$s independently represent a hydrogen atom, a halogen atom, a $C_1$-$C_5$ alkyl group, a $C_1$-$C_4$ alkoxy group, a $C_1$-$C_4$ alkylthio group, a trifluoromethyl group, a $C_1$-$C_4$ haloalkoxy group, a phenyl group, an alkyl-substituted phenyl group, or

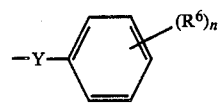

wherein Y represents an oxygen atom or a sulfur atom, $R^6$s independently represent a hydrogen atom, a $C_1$-$C_4$ alkyl group, a $C_1$-$C_4$ alkoxy group, a halogen atom, a nitro group, a cyano group or a trifluoromethyl group and n represents 1 or 2, l represents 0 to 1; and m represents 1, 2 or 3, and fungicidally acceptable adjuvant(s).

7. The fungicidal composition according to claim 6, wherein $R^1$ represents a methyl group; $R^2$ and X represent in combination

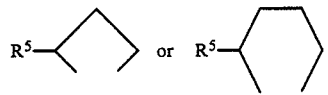

wherein $R^5$ represents a hydrogen atom or a methyl group; $R^3$ represents a hydrogen atom; $R^4$ represents a $C_1$-$C_5$ alkyl group, a $C_1$-$C_4$ alkoxy group, a $C_1$-$C_4$ alkylthio group or a $C_1$-$C_4$ haloalkoxy group, l represents 0; and m represents 1 or 2.

* * * * *